(12) United States Patent
Lacy et al.

(10) Patent No.: US 10,719,581 B2
(45) Date of Patent: Jul. 21, 2020

(54) SYSTEM AND METHOD FOR SECURING THE REMUNERATION OF PATIENT RESPONSIBILITIES FOR HEALTHCARE SERVICES IN A REVENUE MANAGEMENT CYCLE

(71) Applicant: ZirMed, Inc., Louisville, KY (US)

(72) Inventors: James Scott Lacy, Shelbyville, KY (US); Douglas Roy Fielding, Finchville, KY (US); Christopher Lawrence Schremser, New Albany, IN (US)

(73) Assignee: ZirMed, Inc., Louisville, KY (US)

( * ) Notice: Subject to any disclaimer, the term of this patent is extended or adjusted under 35 U.S.C. 154(b) by 458 days.

(21) Appl. No.: 13/963,934

(22) Filed: Aug. 9, 2013

(65) Prior Publication Data
US 2014/0046678 A1    Feb. 13, 2014

Related U.S. Application Data

(60) Provisional application No. 61/681,284, filed on Aug. 9, 2012.

(51) Int. Cl.
| G06Q 30/04 | (2012.01) |
|---|---|
| G06F 19/00 | (2018.01) |
| G06Q 50/22 | (2018.01) |

(52) U.S. Cl.
CPC .......... *G06F 19/328* (2013.01); *G06Q 30/04* (2013.01); *G06Q 50/22* (2013.01)

(58) Field of Classification Search
CPC .............................................. G06C 50/22–24

USPC .......................................................... 705/2–4
See application file for complete search history.

(56) References Cited

U.S. PATENT DOCUMENTS

| 8,280,747 | B1 * | 10/2012 | Sholtis ................. G06F 19/325 |
|---|---|---|---|
| | | | 705/2 |
| 2005/0010438 | A1 | 1/2005 | York et al. |
| 2005/0015280 | A1 | 1/2005 | Gabel et al. |
| 2007/0005403 | A1 | 1/2007 | Kennedy et al. |
| 2007/0011025 | A1 * | 1/2007 | Cracchiolo ............ G06Q 20/10 |
| | | | 705/2 |
| 2007/0011088 | A1 | 1/2007 | Cracchiolo et al. |
| 2007/0027727 | A1 | 2/2007 | Cochrane |
| 2007/0033070 | A1 | 2/2007 | Beck et al. |
| 2007/0043595 | A1 | 2/2007 | Pederson |
| 2007/0050205 | A1 | 3/2007 | Lieberman |

(Continued)

*Primary Examiner* — Michael Tomaszewski
(74) *Attorney, Agent, or Firm* — Michael P. Fortkort; John A. Fortkort; Fortkort & Houston PC

(57) ABSTRACT

A method is provided for obtaining payment for services provided to a patient by a healthcare service provider. The method includes receiving a description (203) of the healthcare services to be provided to the patient by the healthcare service provider; obtaining a cost estimate (205) for the patient responsibility portion of the cost of the healthcare services; and receiving payment authorization (207) from the patient in the amount of the cost estimate along with the payment method information. The payment authorization includes authorization to withdraw funds in the estimated amount from an account associated with the patient. After the healthcare services have been provided to the patient or after all claims relating to the healthcare services have been adjudicated, funds are withdrawn (215) from the account in the authorized amount.

20 Claims, 3 Drawing Sheets

(56) References Cited

U.S. PATENT DOCUMENTS

| | | |
|---|---|---|
| 2007/0061172 A1 | 3/2007 | Lanzalotti |
| 2007/0106607 A1 | 5/2007 | Seib et al. |
| 2007/0179813 A1 | 8/2007 | Darling |
| 2007/0271119 A1* | 11/2007 | Boerger ............... G06F 19/328 705/2 |
| 2007/0299699 A1 | 12/2007 | Policelli et al. |
| 2008/0040155 A1 | 2/2008 | Ray et al. |
| 2008/0195423 A1 | 8/2008 | Baylor et al. |
| 2008/0228641 A1 | 9/2008 | Fredman |
| 2009/0006135 A1 | 1/2009 | Keck et al. |
| 2009/0063197 A1 | 3/2009 | Lisle |
| 2009/0083069 A1* | 3/2009 | Tierney ............... G06F 19/328 705/2 |
| 2009/0094055 A1* | 4/2009 | Gage, Jr. ............. G06F 19/328 705/2 |
| 2009/0157435 A1 | 6/2009 | Seib |
| 2009/0177488 A1 | 7/2009 | Unland et al. |
| 2010/0017235 A1 | 1/2010 | Clubb et al. |
| 2010/0116882 A9 | 5/2010 | Harrison et al. |
| 2010/0138243 A1 | 6/2010 | Carroll |
| 2010/0145810 A1 | 6/2010 | Pourfallah et al. |
| 2010/0185536 A1 | 7/2010 | Rentala et al. |
| 2010/0205090 A1 | 8/2010 | Fellerman |
| 2010/0211416 A1 | 8/2010 | Frank et al. |
| 2010/0332416 A1 | 12/2010 | Visveshwara |
| 2011/0145007 A1 | 6/2011 | Romanini |
| 2011/0251860 A1 | 10/2011 | Boyer et al. |
| 2011/0288881 A1 | 11/2011 | Machani et al. |
| 2011/0295614 A1 | 12/2011 | Hummer et al. |
| 2011/0301972 A1 | 12/2011 | Baylor et al. |
| 2012/0010905 A1 | 1/2012 | Patterson |
| 2012/0035946 A1 | 2/2012 | Coyne |
| 2012/0035952 A1* | 2/2012 | Coyne ................... G06Q 40/08 705/2 |
| 2012/0078646 A1 | 3/2012 | Toleti et al. |
| 2012/0123798 A1 | 5/2012 | Lanzalotti |
| 2012/0173266 A1 | 7/2012 | Brush et al. |
| 2012/0191485 A1 | 7/2012 | Boyer et al. |
| 2012/0233068 A1* | 9/2012 | Epstein ................ G06Q 10/00 705/40 |
| 2012/0239417 A1 | 9/2012 | Pourfallah et al. |
| 2012/0239560 A1 | 9/2012 | Pourfallah et al. |
| 2012/0253852 A1 | 10/2012 | Pourfallah et al. |
| 2012/0296668 A1 | 11/2012 | Meagher |
| 2012/0296815 A1 | 11/2012 | Seib et al. |
| 2012/0303380 A1 | 11/2012 | Baylor et al. |
| 2012/0317036 A1* | 12/2012 | Bower .................. G06Q 20/02 705/75 |
| 2013/0103411 A1 | 4/2013 | Bogle et al. |
| 2013/0179190 A1 | 7/2013 | Boyer et al. |
| 2013/0332199 A1 | 12/2013 | Freiwat et al. |
| 2013/0346100 A1 | 12/2013 | Darling et al. |
| 2014/0088998 A1 | 3/2014 | Boyer et al. |
| 2014/0095194 A1 | 4/2014 | Mahaffey et al. |
| 2014/0149135 A1 | 5/2014 | Boerger et al. |
| 2014/0172445 A1 | 6/2014 | Hajbandeh |
| 2014/0222449 A1 | 8/2014 | Nimmer et al. |
| 2014/0229203 A1 | 8/2014 | Dean et al. |
| 2014/0297307 A1 | 10/2014 | Pletz et al. |
| 2014/0304010 A1 | 10/2014 | Kennedy et al. |
| 2014/0316798 A1 | 10/2014 | Lutzen et al. |
| 2014/0337058 A1 | 11/2014 | Sullivan et al. |
| 2014/0343960 A1 | 11/2014 | Christensen et al. |
| 2014/0350958 A1 | 11/2014 | Saidel et al. |
| 2014/0350959 A1 | 11/2014 | Bogle et al. |

* cited by examiner

SYSTEM AND METHOD FOR SECURING THE REMUNERATION OF PATIENT RESPONSIBILITIES FOR HEALTHCARE SERVICES IN A REVENUE MANAGEMENT CYCLE

CROSS-REFERENCE TO RELATED APPLICATIONS

This application claims priority to U.S. Ser. No. 61/682,755 (Fielding et al.), entitled "SYSTEM AND METHOD FOR SECURING THE REMUNERATION OF PATIENT RESPONSIBILITIES FOR HEALTHCARE SERVICES IN A REVENUE MANAGEMENT CYCLE", which was filed on Aug. 9, 2012, and which is incorporated herein by reference in its entirety.

FIELD OF THE DISCLOSURE

The present disclosure relates generally to healthcare revenue cycle management, and more particularly to systems and methods for securing remuneration for patient responsibilities for healthcare services.

BACKGROUND OF THE DISCLOSURE

Recent changes in the healthcare industry, and in the practices and policies of insurance companies and other healthcare payers, have required patients to pay for an increasing portion of their healthcare costs. In particular, the amounts of healthcare insurance copayments and deductibles have risen dramatically for many patients, even while the coverage afforded by healthcare insurance policies has often decreased.

As a result of the foregoing, the frequency with which healthcare service providers must look to patients for significant portions of healthcare costs has increased, and the average dollar amount of the patient's responsibility for healthcare services has also risen. Consequently, healthcare service providers (and the revenue cycle management companies that work with them) have been forced to spend increasing time and resources on patient collection efforts for services rendered. Patient collections are exceedingly complex due, in part, to the lapse of time between the rendering of services by the healthcare service provider, and the presentation of a patient invoice after the healthcare payer has paid the claim. This process, along with the aforementioned trends in the healthcare industry, have increased transaction costs for healthcare service providers, and have also increased the financial risk associated with failed collection efforts for healthcare service providers.

In some cases, efforts have been made to overcome these problems by estimating the cost of required healthcare services, and then collecting the estimated cost from the patient upfront. However, the legality of this approach is currently being challenged. Moreover, this type of approach requires the availability and ongoing maintenance of a contract management system or fee schedule, which may be overkill for the needs of many organizations.

Another problem with the foregoing approach is that it may create conflicts between revenue cycle management companies and entities such as hospitals, the latter of which frequently have "not-for-profit" mission statements or have prioritized the provision of timely, quality healthcare services over remuneration for those services. In addition, up-front collections, prior to a final determination of patient responsibility, places a financial hardship on many patients.

Upfront collections of this type also pose administrative challenges for healthcare service providers, who must typically return overpayments—or go back to the patient for underpayments—based on insurance determinations that are made after services have been rendered.

SUMMARY OF THE DISCLOSURE

Figure 1:
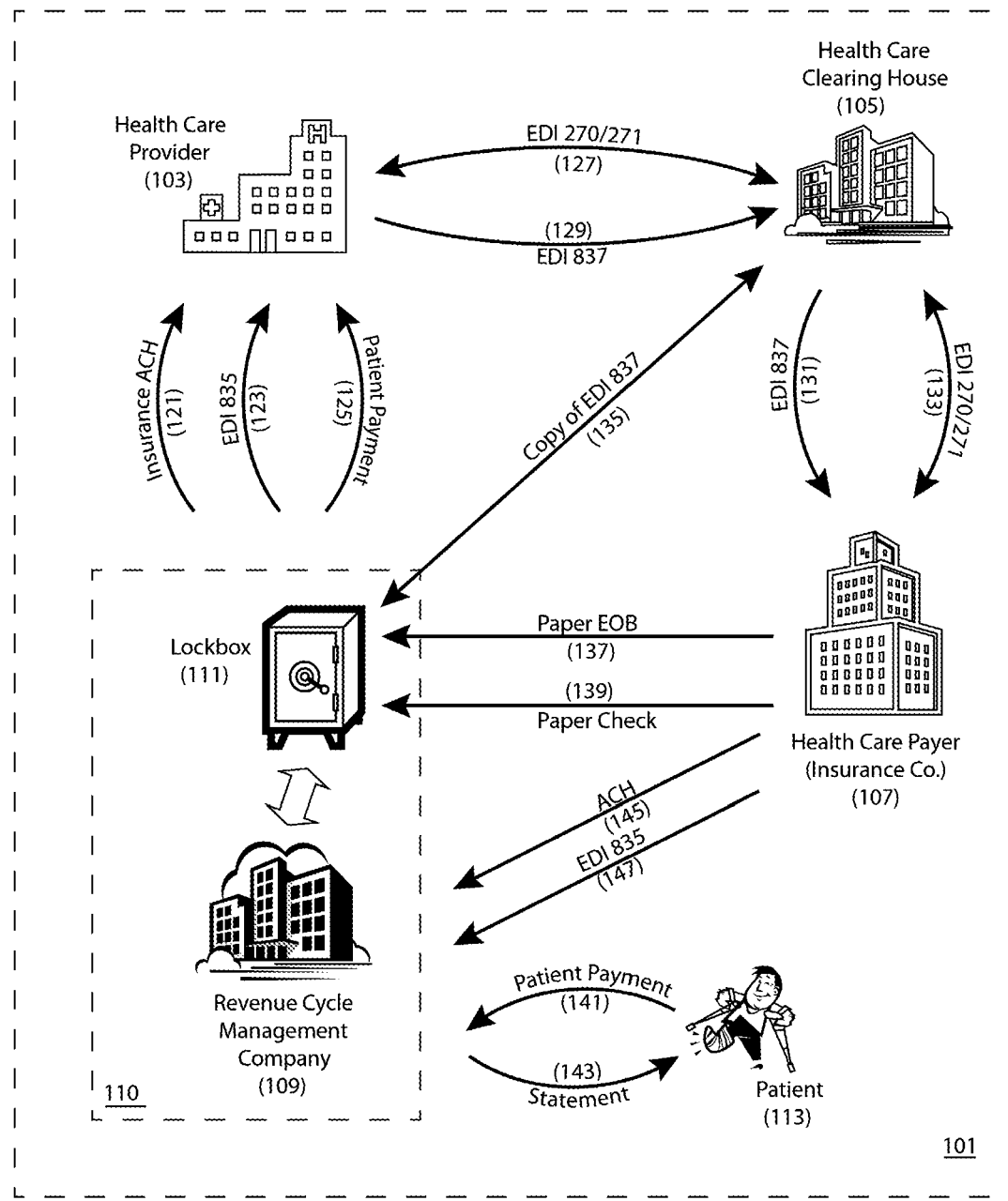
FIG. 1 is an illustration of the entities and transactions involved in a typical revenue cycle in the healthcare industry.

In one aspect, method is provided for securing remuneration for patient responsibilities for healthcare services. The method comprises (a) receiving a description of healthcare services to be provided to a patient by a healthcare service provider; (b) obtaining a cost estimate for the cost of the healthcare services; (c) estimating the patient responsibility portion of this cost; (d) receiving payment authorization from the patient in the amount of the patient responsibility, wherein the payment authorization includes authorization to withdraw funds from an account associated with the patient in the actual patient responsibility amount, so long as this amount falls at or below the authorized amount; (e) obtaining patient payment account information from whence the future payment will come; (f) optionally processing a payment for all or a portion of the patient responsibility amount; and (g) after the healthcare services have been provided, either withdrawing or refunding funds to the account in the actual patient responsibility amount, taking into consideration any funds that may have already been collected prior to service. Preferably, the method further comprises (h) sending the patient a reconciliation receipt for the transaction, and (i) suppressing future patient statements from being delivered to the patient.

In another aspect, a method is provided for processing a payment or refund associated with healthcare services provided to a patient by a healthcare service provider. The method comprises (a) receiving payment authorization from the patient to charge to an account the patient responsibility amount for the healthcare services (and possibly receiving authorization from the patient to refund to the account any overpayment for the patient responsibility amount for the healthcare services); (b) recording any payment collected prior to the provision of the healthcare services; (c) associating a patient statement with the payment authorization; (d) determining, from the associated patient statement, the actual patient responsibility amount for the healthcare services; (e) if the actual patient responsibility amount does not exceed the authorized amount, then processing the payment or refund considering any payment collected prior to service and suppressing the patient statement from being delivered to the patient; and (f) if the actual patient responsibility amount exceeds the authorized amount, then flagging the patient statement for further handling.

In a further aspect, a method is provided for processing a payment or refund for healthcare services provided to a patient by a healthcare service provider. The method comprises (a) receiving payment authorization from the patient to charge to an account the patient responsibility amount for the healthcare services (and possibly receiving authorization from the patient to refund to the account any overpayment for the patient responsibility amount for the healthcare services); (b) recording any payment collected prior to the provision of the healthcare services; (c) associating a remittance with the payment authorization; (d) determining, from the associated remittance, the actual patient responsibility amount for the healthcare services; (e) if the actual patient responsibility amount does not exceed the authorized amount, then processing the payment or refund considering any payment collected prior to the provision of the healthcare services; (f) if the actual patient responsibility amount exceeds the authorized amount, then flagging the remittance for further handling; (g) associating a patient statement with the payment authorization; and (h) if payment has been received by virtue of this process, then suppressing the patient statement from being delivered to the patient.

In still another aspect, a method is provided for obtaining payment for healthcare services provided to a patient by a healthcare service provider. The method comprises (a) receiving a description of the healthcare services to be provided to the patient by the healthcare service provider; (b) obtaining a cost estimate for the cost of the healthcare services; (c) estimating the patient responsibility portion of this cost; (d) receiving payment authorization from the patient in an amount sufficient to cover the cost estimate, wherein the payment authorization includes authorization to withdraw funds up to the authorized amount from an account associated with the patient; (e) receiving an upfront payment from the patient in an amount that partially covers the cost estimate; and after the healthcare services have been provided or after all claims relating to the healthcare services have been adjudicated, (i) if the actual amount of the patient responsibility is greater than the upfront payment, withdrawing funds from the account for the patient responsibility portion in an amount not greater than the authorized amount less the upfront payment, and (ii) if the actual amount of the patient responsibility is less than the upfront payment, refunding to the account the amount of the upfront payment less the actual amount.

In another aspect, a tangible, non-transitory, computer readable medium is provided which contains suitable programming instructions which, when executed by a computational device or a group of computational devices, cause the computational device or group of computational devices to perform any of the foregoing methods.

DETAILED DESCRIPTION

It has now been found that the foregoing needs may be met with the systems and methodologies disclosed herein. In a preferred embodiment of these systems and methodologies, the healthcare services required for a patient are determined upfront, the costs for these services are estimated, and the portion of these costs that the patient will be responsible for is also estimated. Prior to providing the required healthcare services, a payment for all or a portion of the patient responsibility amount may be collected, and authorization is received from the patient to charge the balance of the patient's responsibility (or to credit any overpayment) to a payment account associated with the patient. The revenue cycle management company stores the authorization and the payment method for future presentment. The payment or refund is then processed after the required healthcare services are rendered and/or after the corresponding claim to any relevant insurance companies has been adjudicated (and preferably, after the remittance has been sent by any relevant insurance companies).

The systems and methodologies disclosed herein are advantageous in that they eliminate much of the need for collection or refund efforts on the part of healthcare service providers by identifying payment issues in advance, by obtaining patient payment authorization for the services before the services are rendered, and by obtaining payment method details in advance. Consequently, the healthcare service provider does not have to send a request for payment to the patient or refund checks, but may instead merely send a receipt informing the patient that funds were withdrawn from the patient's account or monies refunded in accordance with the amount agreed upon and authorized by the patient before the healthcare services were rendered.

Moreover, this approach may avoid some of the legal and logistical problems noted above with approaches that require patients to pay in advance for healthcare services, since payment is preferably not processed in the systems and methodologies disclosed herein until after the required services are rendered and/or after the corresponding claim to the insurance company has been adjudicated and the insurance payment has been received, or that refunds are automatically executed in the event that more monies were collected up front than were due.

The systems and methodologies disclosed herein may be better understood by first considering the conventional manner, indicated in FIG. 1, in which claims and remittances are typically handled in the healthcare industry today. The major entities in this system 101 include healthcare service providers 103, clearing houses 105, healthcare payers 107, revenue cycle management companies 109, and patients 113. Each of the revenue cycle management companies 109 may have an associated lockbox 111 (which may be provided by a bank or financial institution) for the receipt of forms and remittance. Of course, it will be appreciated that the depicted system has been simplified for ease of illustration, and that a typical, real-life example of the foregoing type of system may have potentially large numbers of parties of each of the foregoing types.

The healthcare service provider 103 may be, for example, a hospital, a physician's office, an urgent care center, a testing facility or lab, or any other organization that provides healthcare services, treatment, or associated services for patients and then bills for those services. The healthcare payer 107 is typically an insurance company or a related entity that provides insurance coverage for patients.

The revenue cycle management company 109 may be a healthcare information technology company that provides web-based revenue cycle management software solutions for healthcare service providers, and/or may be a healthcare clearing house as defined by HIPAA. Such a company may offer eligibility verification, credit/debit card processing, check processing, claims management, coding compliancy and reimbursement management, patient statements, patient e-commerce, and provider credentialing solutions, as well as electronic remittance advice and patient billing services.

The clearing house 105 is typically an organization that transfers transaction files between the healthcare payer 107 and the healthcare service provider 103. Although depicted in FIG. 1 as a separate entity, in some cases, it may be part of a revenue cycle management company 109.

The interaction between the foregoing entities may be understood by considering the manner in which claims are handled in the healthcare industry. When a healthcare provider 103 provides healthcare services to a patient 113 (such as, for example, treatment of a broken leg), the healthcare provider 103 issues an electronic claim 129 to a healthcare clearinghouse 105 for any portion of the services that were not paid for by the patient 113 at the time the services are rendered. The electronic claim is submitted in a HIPAA-compliant EDI (electronic data interchange) 837 format such as, for example, the HIPAA-compliant X12N 837 version 5010 format. The healthcare provider 103 and the healthcare clearing house 105 also exchange a healthcare eligibility inquiry and response 127 by way of an EDI (electronic data interchange) 270 and 271, respectfully.

The EDI 270 Health Care Eligibility/Benefit Inquiry transaction set is used to request information from a healthcare insurance plan about the coverage afforded by a policy, typically in relation to a particular plan subscriber. The 270 transaction is typically used for inquiries about what services are covered for particular patients (policy subscribers or their dependents), including required copays or coinsurance. It may also be used to inquire about general information on coverage and benefits, or for questions about the coverage of specific benefits for a given plan, such as wheelchair rental information, diagnostic lab services, physical therapy services, and the like. The 270 document typically includes details of the sender of the inquiry (for example, name and contact information of the information receiver), the name of the recipient of the inquiry (that is, the information source), details of the plan subscriber about whom the inquiry is referring, and a description of the eligibility or benefit information requested.

The EDI 271 is the Health Care Eligibility/Benefit Response and is used to transmit the information requested in an EDI 270. The EDI 271 may include such information as eligibility status, maximum benefits (policy limits), exclusions, in-plan/out-of-plan benefits, C.O.B. information, deductibles, co-pays, procedure coverage dates, procedure coverage maximum amount(s) allowed, deductible amount(s), remaining deductible amount(s), co-insurance amount(s), co-pay amount(s), coverage limitation percentages, patient responsibility amount(s) and non-covered amount(s).

The healthcare clearing house 105 then transmits a copy of the EDI 837 131 and the EDI 270/271 Health Care Eligibility/Benefit Inquiry transaction set 133 to the healthcare payer 107, and further transmits a copy of the EDI 837 135 to the revenue cycle management company 110. The healthcare payer 107 then sends paper check payments 139, along with an EOB (Explanation of Benefits) 137, to the revenue cycle management company 110 or to a lockbox 111 associated therewith, or else sends an ACH payment 145 (an electronic payment made through the Automated Clearing House) and electronic remittance advice (ERA) in an EDI 835 147 (currently ANSI X12 835).

The revenue cycle management company 110 sends a statement 143 to the patient 113, and receives payment 141 from the patient 113. The revenue cycle management company 110 then sends any patient payments 125 it receives to the healthcare provider 103. The revenue cycle management company 110 also sends any ACH payments 121 received from the healthcare payer 107, and a copy of the EDI 835 423, to the healthcare provider 103.

It will be appreciated from the foregoing that the typical healthcare revenue cycle involves claims which are submitted to insurance companies or other payers by healthcare service providers, either directly or via a healthcare revenue cycle management company which is associated with the healthcare provider. It will further be appreciated that acknowledgements or responses are received in response to those claims. These responses may contain codifies or textual descriptions of the outcome of the claim. In particular, these responses frequently articulate one or more reasons why the claim is being rejected, but may also include acceptance messages or warning messages relating to a submitted claim.

It will also be appreciated that the system of FIG. 1 entails a financial risk for the healthcare service provider 103 in the amount of the balance that is not paid by the healthcare payer 107 and hence is the responsibility of the patient. As noted above, this risk has been magnified in recent years by rising copayments and deductibles, and by shrinking health insurance coverages. Also, it should be noted that the elapsed time from the patient's initial visit to the final payment on the claim and receipt of the patient statement may be a matter of weeks or months. This often tends to relegate outstanding bills to a non-critical position in the patient's mind.

Figure 2:
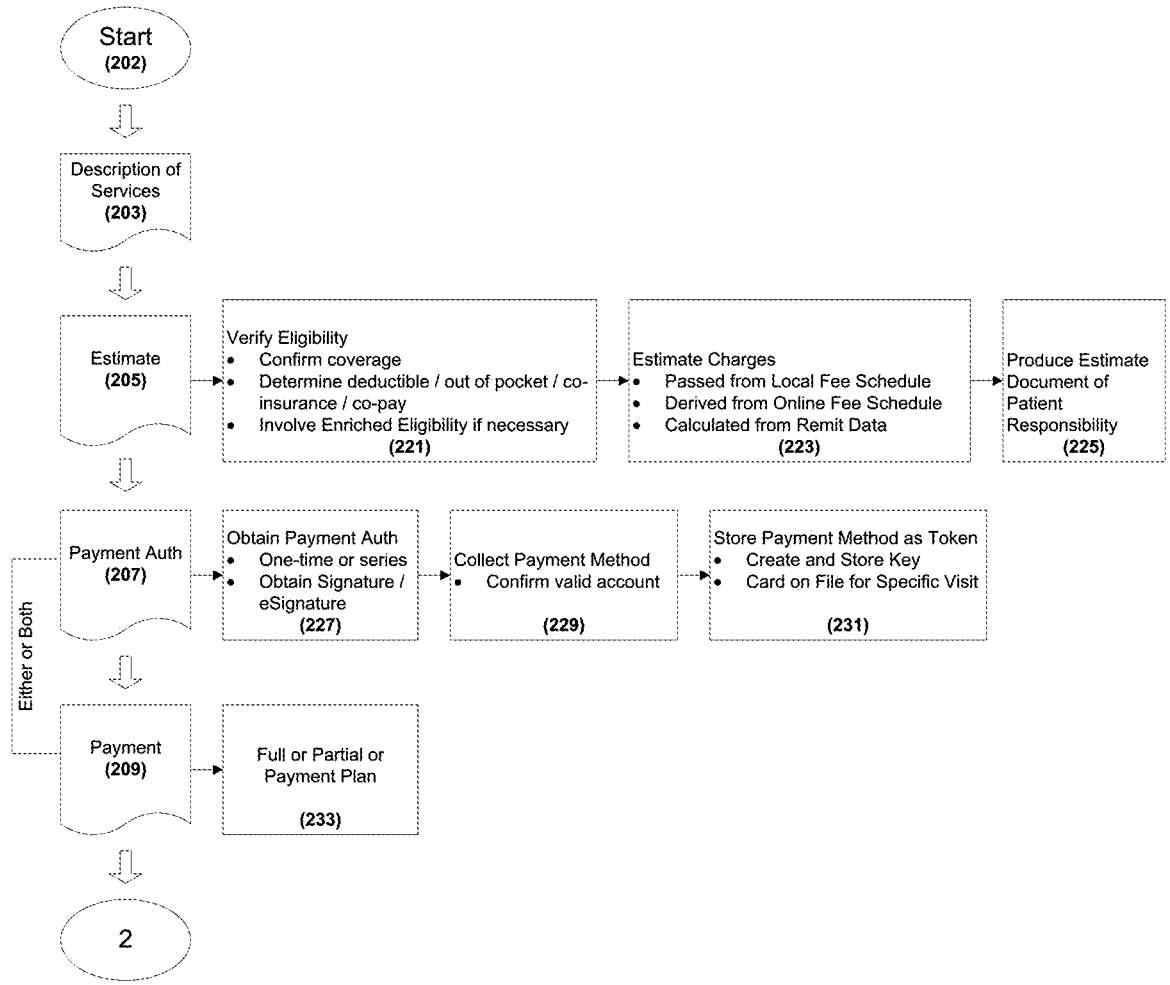
FIGS. 2-3 are illustrations of a first particular, non-limiting embodiment of a process in accordance with the teachings herein.
Figure 3:
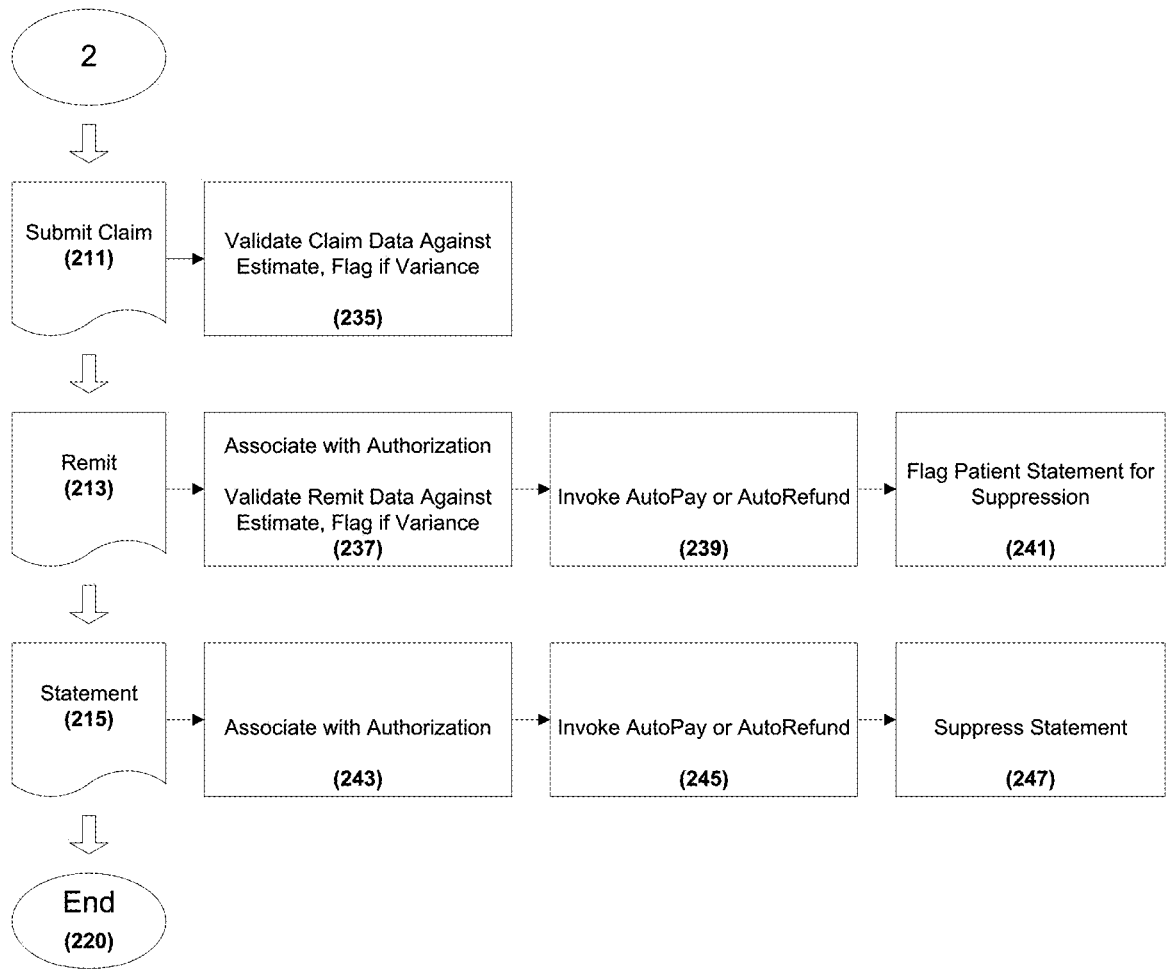

FIGS. 2-3 illustrate a first particular, non-limiting embodiment of a system and methodology in accordance with the teachings herein which may be utilized to mitigate the foregoing risks. In particular, the system 201 depicted therein is designed to help healthcare service providers to improve their collections of patient responsibility amounts by preplanning the services that are going to be provided to the patient, estimating what the patient's responsibility for those services is going to be, and obtaining the patient's authorization upfront (before the healthcare services are provided) to charge a payment account associated with the patient up to a maximum authorized payment amount. In some embodiments, this authorization may also include authorization to refund any overpayments to the account.

The foregoing maximum authorized payment amount is preferably based on the estimated amount of the patient's responsibility, and the payment is processed after the fact (i.e., after the claim has been adjudicated). The account to which payment is charged (or to which any overpayment may be credited) may be, for example, a credit card, a debit card or a checking or savings account.

It will be appreciated from the foregoing that the healthcare service provider does not have to send a statement requesting payment for the planned services, but can instead charge the payment account for the patient responsibility amount (e.g., up to the maximum authorized payment amount) after the services are provided. The healthcare service provider may then send a receipt to the patient confirming that the patient's payment account has been charged or debited in an authorized amount.

In the process depicted in FIGS. 2-3, a database is maintained by a revenue cycle management company. The process commences 202 with the uploading to this database of data relating to future visits by patients to a healthcare service provider. Thus, for example, the uploaded data may relate to next Tuesday's scheduled appointments at a medical practice. The data may be uploaded in batch form or as single data entries, and will typically include information about, and preferably a description of, the services to be provided 203 to a given patient during the patient's scheduled visit. The revenue cycle management company (or a service or business entity affiliated therewith) then submits the planned services to an insurance company or other healthcare payer to verify coverage and obtain benefit information, and receives an EDI transaction back from the healthcare payer.

Ideally, the healthcare payer provides the patient responsibility information (such as, for example, deductibles, remaining deductible, copayments, maximum out-of-pocket amounts, and the like) to the revenue cycle management company. However, when this does not occur, or when the ANSI X12 271 file is incomplete or insufficient, an enriched eligibility process is conducted to determine the insurance coverage eligibility of each patient. The enriched eligibility process preferably involves augmenting the EDI transaction received by the revenue cycle management company from the healthcare payer with additional data which is often available only from the healthcare payer's website.

For example, in a preferred embodiment, after the data from the EDI transaction is received by the revenue cycle management company, an associated service utilizes web bots or other suitable means (if necessary) to screen scrape the healthcare payer's web site, or access the healthcare payer's databases, for additional eligibility information, such as the remaining deductible on a patient's insurance policy, the patient's expected out-of-pocket amount, and other such information which may be helpful or necessary in populating the financial fields in a form or algorithm utilized to establish an estimate of the patient's responsibility for the prospective healthcare services. This additional data is then combined with the data from the EDI transaction to yield enriched eligibility data, which is delivered back to the revenue cycle management company in the standard EDI 271 transaction for eligibility.

Next, the revenue cycle management company prepares an estimate 205 for the cost of the planned services. As part of this process, the eligibility information previously obtained is verified 221, and an estimate is then prepared based on estimated charges 223.

The estimated charges 223 may be derived by various means. In some embodiments, the future visit data file may include the dollar amounts expected for different procedure codes from a fee schedule associated with the healthcare payer. In some variations of this embodiment, the revenue cycle management company may maintain its own online fee schedule and may keep that fee schedule up to date by, for example, automatically updating the fee schedule as fee values are calculated from remittance data or as fee values are passed in from the patient management systems. In other embodiments, the revenue cycle management company may prepare the estimate based on remittance data received for those same procedure codes in historical transactions associated with a healthcare payer. In still other embodiments, the option may exist to override these functions, or to manually enter expected dollar amounts for the purpose of generating the estimate. The estimated patient responsibility amount for the planned healthcare services is determined 225 from the estimated charges.

The revenue cycle management company then obtains payment authorization 207 from the patient for an authorized maximum payment amount based on the estimated patient responsibility amount. The payment authorization may include authorization from the patient for payment in a lump sum or as a series of payments 227 (e.g., pursuant to a monthly payment plan), and it may include an optional upfront payment for any applicable amount towards the total payment. The revenue cycle management company obtains the patient's assent or agreement to the payment authorization by way of a signature (physical or electronic) or by other suitable means.

The revenue cycle management company then collects the relevant payment method 229. This will typically include identification of the account which is to be charged or debited when the payment is processed. Thus, for example, if the account is a credit card, the payment information will typically include the credit card number, the expiration date, the name on the card, the card type (e.g., credit or debit), the card issuer, and possibly a security code associated with the card. This step may also involve confirming the validity of the account to be charged (e.g., by confirming that the account is open and active), and confirming that the remaining credit on the account is sufficient to satisfy the portion of the estimated cost of the healthcare services for which the patient will be responsible. The confirmation of the sufficiency of remaining credit on the account will typically be based on the status quo of the account at the time of the confirmation, although in some embodiments, the available credit in the account may be reduced (possibly as part of the patient's payment authorization) by an amount equal to the patient's estimated responsibility, or this amount may otherwise be blocked off or made unavailable to other charges, to prevent the subsequent charge or debit from being declined due to insufficient funds.

The patient's payment method is then stored in a database maintained by the revenue cycle management company as a token 231 with an associated key. The token may be transaction specific (for example, it may be specific for the healthcare services associated with the estimate), or it may be utilized for any future healthcare activities associated with the patient. Depending on the nature of the token, the associated key may be, for example, a shared key, a session key, a content encryption key, a traffic encryption key, or a multicast key. At this time, prior to services, the patient may make a payment which may be a full or partial payment towards the total payment.

Subsequent to payment authorization 207, the patient receives the healthcare services for which the estimate was generated. At that time, the patient may make a payment 209, which may be a full or partial payment 233, towards the total payment. In the event that the patient makes a full payment, payment authorization may not be required. However, in some embodiments, payment information may nonetheless be collected and stored in case refunds are needed.

Several modifications and variations are possible with respect to the systems and methodologies described. For example, in some embodiments, an additional "check-out" step or procedure may be added to the process to provide a means by which the description of the healthcare services (e.g., including the cost estimate for the planned services, the payment authorization, or both) may be refined. The need for such refinement may occur, for example, due to some services having been added, withheld or modified at the time that the healthcare services were actually rendered.

In the event that the description of the healthcare services is modified during the check-out process, several different outcomes are possible. In some embodiments, the payment may be processed so long as the actual cost of the healthcare services does not exceed the cost estimate or the maximum authorized payment amount. In such embodiments, an appropriate document may be issued which explains any differences between the planned healthcare services and the healthcare services which were actually provided.

Next, a claim is submitted 211 to the insurance company or other healthcare payer for the rendered healthcare services, remittance 213 is received from the healthcare payer, a statement 215 is generated, the remittance 213 is associated 237 with the authorization or the statement 215 is associated 243 with the authorization, and automatic payment 239, 245 for the patient responsibility portion of the cost of the healthcare services is triggered from the patient's payment account on the basis of the payment authorization previously received from the patient. If the final patient responsibility amount ends up being less than any amounts that may have been collected prior to service or at time of service, a refund may be issued to the patient using the payment methods collected at time the estimate was generated.

These steps are centered around the ability of the revenue cycle management company—made possible by the payment authorization received from the patient—to automatically invoke the payment authorization and automatically process the payment from the patient or refund back to the patient by virtue of the fact that a remittance was received from the healthcare payer by the revenue cycle management company. Consequently, when the revenue cycle management company receives a remittance, it is able to link the remittance to a cost estimate for the healthcare services and a payment authorization for those healthcare services provided by the patient, and may then effect a payment or refund transaction.

The claim submission process 211 may include a claim validation step 235 in which the claim is validated against the cost estimate for the healthcare services. The claim may be flagged if there is a variance between the actual and estimated cost of the provided healthcare services, or if the variance exceeds a certain threshold. Various linkage data may be provided for linking the claim to the patient. This linkage data may include, for example, the patient's name and account number, the amount of the claim and/or the estimated cost, the maximum authorized payment amount, and any relevant insurance information or process codes.

When the remittance 213 is received from the healthcare payer by the revenue cycle management company, the remittance is associated with the payment authorization 237. The remittance as received is then compared to the estimated remittance and is validated if it is in agreement with the estimate (e.g., if the estimate is a range, the remittance as received is validated if it falls within the range). If there is a variance between the remittance as received and the estimate, or if the variance exceeds a certain threshold, the remittance may be flagged for further action before further processing and may be identified for action in a workflow location for review and appropriate action.

If there are no issues with the remittance that require further action, automatic payment of the patient's responsibility is invoked 239 or a refund generated, based on the payment authorization 207 received from the patient before services were provided and considering any payments collected prior to (or at) the time of service. The payment token 231 may be presented to the process workflow as part of the automatic payment 239, and will preferably induce the suppression 241, 247 of the patient statement from being mailed. The process then terminates 220.

It will be appreciated that, in the foregoing process, the revenue cycle management company may also charge the patient when the statement is received and/or suppressed. The patient may also be charged when the remittance is received, in which case the statement may be suppressed when generated by the healthcare service provider and transmitted to the revenue cycle management company.

In other embodiments (or in variations of the foregoing embodiments), the payment authorization may be itemized, with the patient agreeing to pay for any item in the planned healthcare services whose cost does not exceed the estimated cost for that item (or whose cost does not exceed a maximum authorized payment amount for the item). In such embodiments, payment may be processed for any items appearing in the planned healthcare services whose cost does not exceed the itemized cost for that item set forth in the estimate (or whose cost does not exceed a maximum authorized payment amount for the item), and the patient, healthcare payer or other appropriate entity may be invoiced for any remaining or unpaid items.

In still other embodiments (or in variations of the foregoing embodiments), the cost estimate may be revised in light of the differences between the planned and provided healthcare services, and this revised cost estimate may be utilized to obtain a revised payment authorization from the patient. In some implementations of this embodiment, a revised cost estimate and a revised payment authorization may be obtained before the healthcare services are rendered. In other implementations, the differences between the planned and provided healthcare services may cause the claim or remittance to be flagged for further processing.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A computer-implemented method for processing a payment or a refund for healthcare services provided to each of a plurality of patients by one or more healthcare service providers, the computer-implemented method comprising:
    maintaining in a database associated with the one or more healthcare service providers information about one or more types of scheduled appointments at the one or more healthcare service providers, said information including a description of the healthcare services to be provided to a prospective patient during said one or more types of scheduled appointments at the one or more healthcare service providers, and a fee associated with said description; and
    performing electronically, for each patient of the plurality of patients, the steps of:
    (a) uploading data to a database maintained by a revenue cycle management company from the database associated with the one or more healthcare service providers to obtain a description of and a fee for potential healthcare services to be provided to said each patient of the plurality of patients by the one or more healthcare service providers during an upcoming visit by said each patient of the plurality of patients to the one or more healthcare service providers,
    (b) submitting a benefit inquiry transaction set to request information from one or more third-party healthcare payers regarding coverage afforded to said each patient of the plurality of patients for the description of potential healthcare services to be provided to said each patient of the plurality of patients by the one or more healthcare service providers during the upcoming visit by said each patient of the plurality of patients to the one or more healthcare service providers,
    (c) receiving a response from the one or more third party healthcare payers to the benefit inquiry transaction set, which response includes information regarding said coverage afforded to said each patient of the plurality of patients for the description of potential healthcare services to be provided to said each patient of the plurality of patients by the one or more healthcare service providers during the upcoming visit by said each patient of the plurality of patients to the one or more healthcare service providers,
    (d) conducting an enriched eligibility process to determine additional eligibility information regarding coverage afforded to said each patient of the plurality of patients for the description of potential healthcare services to be provided to said each patient of the plurality of patients by the one or more healthcare service providers during the upcoming visit by said each patient of the plurality of patients to the one or more healthcare service providers;

(e) said conducting the enriched eligibility process further comprising screen scraping one or more websites for said one or more healthcare payers by utilizing one or more web bots to screen scrape the one or more websites to determine the additional eligibility information, said additional eligibility information including a remaining deductible on a patient's insurance policy, a patient's expected out-of-pocket amount and other information that may be helpful or necessary to populate one or more financial fields in a form or an algorithm utilized to establish an estimate of the patient's responsibility portion for the description of potential healthcare services to be provided to said each patient of the plurality of patients by the one or more healthcare service providers during the upcoming visit by said each patient of the plurality of patients to the one or more healthcare service providers;

(f) combining the additional eligibility information with the information received from the healthcare payer in response to the benefit inquiry transaction set to create enriched eligibility data;

(g) calculating a cost estimate for a cost of the potential healthcare services to be provided to said each patient of the plurality of patients by the one or more healthcare service providers during said upcoming visit by said each patient of the plurality of patients to said one or more healthcare service providers based on the description of the healthcare services to be potentially provided to said each patient of the plurality of patients by the one or more healthcare service providers during the upcoming visit by said each patient of the plurality of patients, and the fee associated therewith, which description and fee are included in the data uploaded from said database maintained for the one or more healthcare service providers, (h) determining a patient responsibility portion of the cost estimate for said each patient of the plurality of patients, which said patient responsibility portion equals an amount estimated that said each patient of the plurality of patients would be expected to financially bear after calculating any potential payments that might be made by one or more third party healthcare payers, based on the coverage included in the enriched eligibility data, which payments might be made by the one or more third party healthcare service providers on behalf of said each patient of the plurality of patients for the potential healthcare services to be provided to said each patient of the plurality of patients by the one or more healthcare service providers during the upcoming visit by said each patient of the plurality of patients to the one or more healthcare service providers, (i) obtaining patient payment account information from said each patient of the plurality of patients, said patient payment account information including one or more accounts associated with said each patient of the plurality of patients from whence one or more future payments may be authorized by said each patient of the plurality of patients for actual healthcare services provided by the one or more healthcare service providers during the upcoming visit to the one or more healthcare service providers by said each patient of the plurality of patients, (j) receiving a payment authorization from said each patient of the plurality of patients before the actual healthcare services are rendered by the one or more healthcare service providers during the upcoming visit by said each patient of the plurality of patients to the one or more healthcare service providers, said payment authorization being in an authorized amount sufficient to cover the patient responsibility portion of the cost estimate for said each patient of the plurality of patients, wherein the payment authorization includes patient authorization by said each patient of the plurality of patients to withdraw funds up to the authorized amount sufficient to cover the patient responsibility portion of the cost estimate from the one or more accounts associated with said each patient of the plurality of patients, so long as an actual amount withdrawn from the one or more accounts associated with said each patient of the plurality of patients equals or falls below the authorized amount, (k) receiving patient authorization from said each patient of the plurality of patients to refund to the one or more accounts associated with said each patient of the plurality of patients any overpayment for the patient responsibility amount for the actual healthcare services provided by the one or more healthcare service providers to said each patient of the plurality of patients during the actual visit by said each patient of the plurality of patients to the one or more healthcare service providers, (l) recording electronically for the one or more healthcare service providers any payment collected by the one or more healthcare service providers prior to providing the actual healthcare services by the one or more healthcare service providers to said each patient of the plurality of patients during the upcoming visit by said each patient of the plurality of patients to the one or more healthcare providers;

(m) associating electronically a patient statement with said each patient of the plurality of patients for the actual healthcare services provided by the one or more healthcare service providers to said each patient of the plurality of patients during the actual visit by said each patient of the plurality of patients to the one or more healthcare service providers, (n) submitting electronically a patient statement to one or more third party healthcare payers on behalf of said each patient of the plurality of patients for the actual healthcare services provided to said each patient of the plurality of patients during the actual visit by said each patient of the plurality of patients to the one or more healthcare service providers, (o) associating and recording electronically with the payment authorization of said each patient of the plurality of patients any remittance received from said one or more third party healthcare payers on behalf of said each patient of the plurality of patients for the actual healthcare services provided to said each patient of the plurality of patients during the actual visit by said each patient of the plurality of patients to the one or more healthcare service providers, (p) determining an actual patient responsibility amount for said each patient of the plurality of patients for the actual healthcare services provided by the one or more healthcare service providers during the actual visit by said each patient of the plurality of patients to the one or more healthcare service providers based on said any remittance associated with the payment authorization of said each patient of the plurality of patients, said remittance being received from said one or more third party healthcare payers on behalf of said each patient of the plurality of patients for the actual healthcare services provided to said each patient of the plurality of patients during the actual visit by said each patient of the plurality of patients to the one or more healthcare service providers, (q) withdrawing electronically funds from the one or more accounts associated with said each patient of the plurality of patients after the actual healthcare services have been provided by the one or more healthcare service providers during the actual visit by said each patient of the plurality of patients to the one or more healthcare service providers, or after all claims relating to the actual healthcare services provided by the one or more healthcare service providers during the actual visit by said each patient of the plurality of patients to the one or more healthcare service providers have been adjudicated, said funds being withdrawn electronically being in an amount not greater than the authorized amount authorized by said each patient of the plurality of patients, taking into consideration said any payment recorded for the one or more healthcare service providers prior to providing the actual healthcare services by the one or more healthcare service providers to said each patient of the plurality of patients, or refunding funds electronically to the one or more accounts associated with said each patient of the plurality of patients, if said any payment recorded for the one or more healthcare service providers prior to providing the actual healthcare services to said each patient of the plurality of patients exceeds an actual patient responsibility portion, (r) suppressing the patient statement associated with said each patient of the plurality of patients for the actual healthcare services provided by the one or more healthcare service providers to said each patient of the plurality of patients during the actual visit by said each patient of the plurality of patients to the one or more healthcare service providers from being delivered to said each patient of the plurality of patients, if the actual patient responsibility amount fails to exceed the authorized amount, (s) flagging electronically for further handling the patient statement associated with said each patient of the plurality of patients for the actual healthcare services provided by the one or more healthcare service providers to said each patient of the plurality of patients during the actual visit by said each patient of the plurality of patients to the one or more healthcare service providers, if the actual patient responsibility amount exceeds the authorized amount authorized by said each patient of the plurality of patients, and (t) sending electronically, only after funds are withdrawn, a receipt informing said each patient of the plurality of patients that funds were withdrawn from the one or more accounts associated with said each patient of the plurality of patents in accordance with the authorized amount authorized by said each patient of the plurality of patients before the actual healthcare services were rendered by the one or more healthcare service providers to said each patient of the plurality of patients during the actual visit by said each patient of the plurality of patients to the one or more healthcare service providers, and (u) sending electronically, only after funds are refunded, a receipt informing said each patient of the plurality of patients that funds were refunded to the one or more accounts associated with said each patient of the plurality of patents in accordance with the authorized amount authorized by said each patient of the plurality of patients before the actual healthcare services were rendered by the one or more healthcare service providers to said each patient of the plurality of patients during the actual visit by said each patient of the plurality of patients to the one or more healthcare service providers;

wherein steps (a)-(u) are performed by a computer of the revenue cycle management company that submits one or more healthcare claims to one or more healthcare payers on behalf of said one or more healthcare service providers and receives remittances from said one or more healthcare payers in response to said one or more healthcare claims submitted to the one or more healthcare payers on behalf of said one or more healthcare service providers.

2. The computer-implemented method of claim 1, wherein obtaining a cost estimate includes retrieving data from a fee schedule associated with the one or more healthcare service providers or the one or more third party healthcare payers.

3. The computer-implemented method of claim 2, wherein the fee schedule is maintained by data from past remittances received from the one or more third party healthcare payers.

4. The computer-implemented method of claim 1, wherein calculating a cost estimate includes estimating the costs associated with the prospective healthcare services based on past remittances received from the one or more third party healthcare payers for the described healthcare services.

5. The computer-implemented method of claim 1, wherein receiving payment authorization includes receiving a digital indication of consent for the payment, and wherein said digital indication of consent includes (a) an electronic signature, or (b) the selection, by the patient, of a field indicating consent, and wherein the field is rendered on a monitor by a software program.

6. The computer-implemented method of claim 1, wherein the account information is stored in an electronic token associated with said each patient of the plurality of patients.

7. The computer-implemented method of claim 6, wherein the electronic token further includes a session key or a shared key to be used in withdrawing funds from the account in the authorized amount.

8. The computer-implemented method of claim 1, further comprising for each patient of the plurality of patients:
   comparing the description of the healthcare services received from the one or more healthcare service providers to the healthcare services actually provided by the one or more healthcare service providers, thereby identifying any differences between the two; and
   adjusting the estimated amount to account for the differences.

9. The computer-implemented method of claim 8, further comprising for each patient of the plurality of patients:

adjusting the payment authorization to reflect the change in services.

10. The computer-implemented method of claim 8, wherein the payment authorization is adjusted only if the adjusted estimated amount is not greater than the original cost estimate.

11. A tangible, non-transitory, computer readable medium which contains suitable programming instructions which, when executed by a computational device or a group of computational devices, cause the computational device or group of computational devices to perform the steps of:

maintaining in a database associated with the one or more healthcare service providers information about one or more types of scheduled appointments at the one or more healthcare service providers, said information including a description of the healthcare services to be provided to a prospective patient during said one or more types of scheduled appointments at the one or more healthcare service providers, and a fee associated with said description, performing electronically, for each patient of the plurality of patients:

(a) uploading data to a database maintained by a revenue cycle management company from the database associated with the one or more healthcare service providers to obtain a description of and a fee for potential healthcare services to be provided to said each patient of the plurality of patients by the one or more healthcare service providers during an upcoming visit by said each patient of the plurality of patients to the one or more healthcare service providers, (b) submitting a benefit inquiry transaction set to request information from one or more third-party healthcare payers regarding coverage afforded to said each patient of the plurality of patients for the description of potential healthcare services to be provided to said each patient of the plurality of patients by the one or more healthcare service providers during the upcoming visit by said each patient of the plurality of patients to the one or more healthcare service providers, (c) receiving a response from the one or more third party healthcare payers to the benefit inquiry transaction set, which response includes information regarding said coverage afforded to said each patient of the plurality of patients for the description of potential healthcare services to be provided to said each patient of the plurality of patients by the one or more healthcare service providers during the upcoming visit by said each patient of the plurality of patients to the one or more healthcare service providers, (d) conducting an enriched eligibility process to determine additional eligibility information regarding coverage afforded to said each patient of the plurality of patients for the description of potential healthcare services to be provided to said each patient of the plurality of patients by the one or more healthcare service providers during the upcoming visit by said each patient of the plurality of patients to the one or more healthcare service providers;

(e) said conducting the enriched eligibility process further comprising screen scraping one or more websites for said one or more healthcare payers by utilizing one or more web bots to screen scrape the one or more websites to determine the additional eligibility information, said additional eligibility information including a remaining deductible on a patient's insurance policy, a patient's expected out-of-pocket amount and other information that may be helpful or necessary to populate one or more financial fields in a form or an algorithm utilized to establish an estimate of the patient's responsibility portion for the description of potential healthcare services to be provided to said each patient of the plurality of patients by the one or more healthcare service providers during the upcoming visit by said each patient of the plurality of patients to the one or more healthcare service providers;

(f) combining the additional eligibility information with the information received from the healthcare payer in response to the benefit inquiry transaction set to create enriched eligibility data;

(g) calculating a cost estimate for a cost of the potential healthcare services to be provided to said each patient of the plurality of patients by the one or more healthcare service providers during said upcoming visit by said each patient of the plurality of patients to said one or more healthcare service providers based on the description of the healthcare services to be potentially provided to said each patient of the plurality of patients by the one or more healthcare service providers during the upcoming visit by said each patient of the plurality of patients, and the fee associated therewith, which description and fee are included in the data uploaded from said database maintained for the one or more healthcare service providers, (h) determining a patient responsibility portion of the cost estimate for said each patient of the plurality of patients, which said patient responsibility portion equals an amount estimated that said each patient of the plurality of patients would be expected to financially bear after calculating any potential payments that might be made by one or more third party healthcare payers, based on the coverage included in the enriched eligibility data, which payments might be made by the one or more third party healthcare service providers on behalf of said each patient of the plurality of patients for the potential healthcare services to be provided to said each patient of the plurality of patients by the one or more healthcare service providers during the upcoming visit by said each patient of the plurality of patients to the one or more healthcare service providers, (i) obtaining patient payment account information from said each patient of the plurality of patients, said patient payment account information including one or more accounts associated with said each patient of the plurality of patients from whence one or more future payments may be authorized by said each patient of the plurality of patients for actual healthcare services provided by the one or more healthcare service providers during the upcoming visit to the one or more healthcare service providers by said each patient of the plurality of patients, (j) receiving a payment authorization from said each patient of the plurality of patients before the actual healthcare services are rendered by the one or more healthcare service providers during the upcoming visit by said each patient of the plurality of patients to the one or more healthcare service providers, said payment authorization being in an authorized amount sufficient to cover the patient responsibility portion of the cost estimate for said each patient of the plurality of patients, wherein the payment authorization includes patient authorization by said each patient of the plurality of patients to withdraw funds up to the authorized amount sufficient to cover the patient responsibility portion of the cost estimate from the one or more accounts associated with said each patient of the plurality of patients, so long as an actual amount withdrawn from the one or more accounts associated with said each patient of the plurality of patients equals or falls below the authorized amount, (k) receiving patient authorization from said each patient of the plurality of patients to refund to the one or more accounts associated with said each patient of the plurality of patients any overpayment for the patient responsibility amount for the actual healthcare services provided by the one or more healthcare service providers to said each patient of the plurality of patients during the actual visit by said each patient of the plurality of patients to the one or more healthcare service providers, (l) recording electronically for the one or more healthcare service providers any payment collected by the one or more healthcare service providers prior to providing the actual healthcare services by the one or more healthcare service providers to said each patient of the plurality of patients during the upcoming visit by said each patient of the plurality of patients to the one or more healthcare providers;

(m) associating electronically a patient statement with said each patient of the plurality of patients for the actual healthcare services provided by the one or more healthcare service providers to said each patient of the plurality of patients during the actual visit by said each patient of the plurality of patients to the one or more healthcare service providers, (n) submitting electronically a patient statement to one or more third party healthcare payers on behalf of said each patient of the plurality of patients for the actual healthcare services provided to said each patient of the plurality of patients during the actual visit by said each patient of the plurality of patients to the one or more healthcare service providers, (o) associating and recording electronically with the payment authorization of said each patient of the plurality of patients any remittance received from said one or more third party healthcare payers on behalf of said each patient of the plurality of patients for the actual healthcare services provided to said each patient of the plurality of patients during the actual visit by said each patient of the plurality of patients to the one or more healthcare service providers, (p) determining an actual patient responsibility amount for said each patient of the plurality of patients for the actual healthcare services provided by the one or more healthcare service providers during the actual visit by said each patient of the plurality of patients to the one or more healthcare service providers based on said any remittance associated with the payment authorization of said each patient of the plurality of patients, said remittance being received from said one or more third party healthcare payers on behalf of said each patient of the plurality of patients for the actual healthcare services provided to said each patient of the plurality of patients during the actual visit by said each patient of the plurality of patients to the one or more healthcare service providers, (q) withdrawing electronically funds from the one or more accounts associated with said each patient of the plurality of patients after the actual healthcare services have been provided by the one or more healthcare service providers during the actual visit by said each patient of the plurality of patients to the one or more healthcare service providers, or after all claims relating to the actual healthcare services provided by the one or more healthcare service providers during the actual visit by said each patient of the plurality of patients to the one or more healthcare service providers have been adjudicated, said funds being withdrawn electronically being in an amount not greater than the authorized amount authorized by said each patient of the plurality of patients, taking into consideration said any payment recorded for the one or more healthcare service providers prior to providing the actual healthcare services by the one or more healthcare service providers to said each patient of the plurality of patients, or refunding funds electronically to the one or more accounts associated with said each patient of the plurality of patients, if said any payment recorded for the one or more healthcare service providers prior to providing the actual healthcare services to said each patient of the plurality of patients exceeds an actual patient responsibility portion, (r) suppressing the patient statement associated with said each patient of the plurality of patients for the actual healthcare services provided by the one or more healthcare service providers to said each patient of the plurality of patients during the actual visit by said each patient of the plurality of patients to the one or more healthcare service providers from being delivered to said each patient of the plurality of patients, if the actual patient responsibility amount fails to exceed the authorized amount, (s) flagging electronically for further handling the patient statement associated with said each patient of the plurality of patients for the actual healthcare services provided by the one or more healthcare service providers to said each patient of the plurality of patients during the actual visit by said each patient of the plurality of patients to the one or more healthcare service providers, if the actual patient responsibility amount exceeds the authorized amount authorized by said each patient of the plurality of patients, and (t) sending electronically, only after funds are withdrawn, a receipt informing said each patient of the plurality of patients that funds were withdrawn from the one or more accounts associated with said each patient of the plurality of patents in accordance with the authorized amount authorized by said each patient of the plurality of patients before the actual healthcare services were rendered by the one or more healthcare service providers to said each patient of the plurality of patients during the actual visit by said each patient of the plurality of patients to the one or more healthcare service providers, and (u) sending electronically, only after funds are refunded, a receipt informing said each patient of the plurality of patients that funds were refunded to the one or more accounts associated with said each patient of the plurality of patents in accordance with the authorized amount authorized by said each patient of the plurality of patients before the actual healthcare services were rendered by the one or more healthcare service providers to said each patient of the plurality of patients during the actual visit by said each patient of the plurality of patients to the one or more healthcare service providers;

wherein steps (a)-(u) are performed by a computer of the revenue cycle management company that submits one or more healthcare claims to one or more healthcare payers on behalf of said one or more healthcare service providers and receives remittances from said one or more healthcare payers in response to said one or more healthcare claims submitted to the one or more healthcare payers on behalf of said one or more healthcare service providers.

12. The tangible, non-transitory, computer readable medium of claim 11, wherein the estimate is a numerical range, wherein the payment is processed if the payment responsibility amount falls within the numerical range, and wherein processing the payment includes withdrawing funds from the account in the actual patient responsibility amount.

13. The tangible, non-transitory, computer readable medium of claim 12, wherein the steps further comprise:
flagging for suppression any future patient statements received for the healthcare services provided to said each patient of the plurality of patients and to which the payment authorization applies.

14. The tangible, non-transitory, computer readable medium of claim 12, wherein the healthcare services pertain to a single visit to the one or more healthcare service providers, and the steps further comprise flagging for suppression any future patient statements received for the healthcare services provided to the patient during that visit.

15. The tangible, non-transitory, computer readable medium of claim 12, wherein the steps further comprise:
receiving a patient statement for the healthcare services; and suppressing the patient statement from processing.

16. The tangible, non-transitory, computer readable medium of claim 11, wherein the steps further comprise:
receiving a description of the healthcare services to be provided to said each patient of the plurality of patients by the one or more healthcare service providers.

17. The tangible, non-transitory, computer readable medium of claim 11, wherein the remittance is received from an insurance company.

18. The tangible, non-transitory, computer readable medium of claim 11, wherein payment authorization is received before the healthcare services are provided to the patient.

19. The tangible, non-transitory, computer readable medium of claim 11, wherein the payment authorization is limited to healthcare services provided during a single visit to the one or more healthcare service providers.

20. The computer implemented method of claim 1, further comprising:
comparing the description of the healthcare services received from the one or more healthcare service providers to the healthcare services actually provided by the one or more healthcare service providers, thereby identifying any differences between the two;
adjusting the estimated amount to account for the differences; and
adjusting the payment authorization to reflect the change in services;
wherein receiving payment authorization includes receiving account information from the each patient of the plurality of patients for an account to be charged for the healthcare services after the healthcare services are rendered;
wherein the account information is stored in an electronic token associated with the each patient of the plurality of patients;
wherein obtaining a cost estimate includes estimating the costs associated with the healthcare services based on past remittances received from a plurality of healthcare payers for the described healthcare services;
wherein receiving payment authorization includes receiving a digital indication of consent for the payment, and wherein said digital indication of consent includes (a) an electronic signature, or (b) the selection, by the each patient of the plurality of patients, of a field indicating consent, and wherein the field is rendered on a monitor by a software program;
wherein obtaining a cost estimate includes retrieving data from a fee schedule associated with one or more healthcare service providers or one or more healthcare payers; and
wherein the fee schedule is maintained by data from past remittances received from one or more healthcare payers.

* * * * *